United States Patent [19]

Zema et al.

[11] Patent Number: 5,306,506
[45] Date of Patent: Apr. 26, 1994

[54] PHARMACEUTICAL COMPOSITION FOR RAPID SUSPENSION IN WATER

[75] Inventors: Marco Zema, Como; Luigi G. Mapelli; Marco G. Marconi, both of Milan, all of Italy

[73] Assignee: Eurand International S.p.A., Milan, Italy

[21] Appl. No.: 838,818

[22] PCT Filed: Jul. 4, 1991

[86] PCT No.: PCT/EP91/01268
§ 371 Date: Mar. 3, 1992
§ 102(e) Date: Mar. 3, 1992

[87] PCT Pub. No.: WO92/00731
PCT Pub. Date: Jan. 23, 1992

[30] Foreign Application Priority Data

Jul. 11, 1990 [IT] Italy .................. 20908 A/90

[51] Int. Cl.⁵ .................................. A61K 9/46
[52] U.S. Cl. ............................ 424/466; 424/489; 424/490; 424/493; 424/494; 514/777; 514/778; 514/779; 514/781; 514/782; 514/784
[58] Field of Search .......... 424/466, 489, 490, 493, 424/494

[56] References Cited

U.S. PATENT DOCUMENTS 4,806,358  2/1989  Khan et al. .................. 424/466
4,888,177  12/1989  Gergely et al. .............. 424/466

*Primary Examiner*—Thurman K. Page
*Assistant Examiner*—James M. Spear
*Attorney, Agent, or Firm*—Adley F. Mandel

[57] ABSTRACT

The invention provides a solid pharmaceutical composition for addition to water to produce a suspension of a drug comprising (a) a drug which is substantially water-insoluble or microencapsulated; (b) a thickening or suspending agent; (c) a pharmaceutically acceptable acid; (d) a pharmaceutically acceptable carbonate or bicarbonate; characterised in that the weight ratio of c+d:b is from 1:1.5 to 1:15 and the amount of c+d is sufficient to obtain rapid hydration of the thickening or suspending agent (b) when the composition is mixed with water such that a homogeneous suspension of the drug is obtained within 30 seconds. A method for preparing the composition is also described.

19 Claims, No Drawings

PHARMACEUTICAL COMPOSITION FOR RAPID SUSPENSION IN WATER

The present invention relates to a pharmaceutical formulation suitable for the administration of drugs and in particular of microcapsules of drugs in a monodose sachet form, the contents of which are poured into water at the moment of use. A process for preparing the formulation is also included.

In the description and the claims which follow we will use mostly the terms microcapsules or microencapsulated drugs, but the present invention can also be applied to solid drug particles (powders, crystals, granules) which are insoluble or slightly soluble in water or drinkable aqueous liquids (milk, fruit juices, etc.) and of which one desires to obtain an extemporary and homogeneous suspension.

In the following description and claims the term:
"microcapsule" is used to indicate drug particles, powders, crystals, granules, pellets and also liquid drops, coated in a polymeric membrane
"microencapsulation" is generically the process used for the application of a membrane
"packet or monodose sachet" is a container which contains a single dose of drug plus the excipients of the formulation
"thickening or suspending substances" are substances which dissolve in water and which increase in density and viscosity allowing solid particles to be suspended.

Microencapsulation is a process known from some time and consists of coating substances with a continuous film based on natural or synthetic polymers.

The processes of microencapsulation are numerous. Many of these and the relative patents are cited and described in the volumes "Microcapsules and Microencapsulation Techniques" (published in 1976) and "Microcapsules and other Capsules. Advance since 1975" (published in 1979) both by M. H. Guttcho. Among the preferred processes are those described in the U.S. Pat. Nos. 3,196,827 and 3,253,944 by D. E. Wurster which describe methods of mechanical coating consisting of spraying a membrane around particles using suitable apparatus, and those cited in U.S. Pat. Nos. 3,415,758, 3,155,590 and 3,341,416 which described methods of chemicophysical coating based on the coacervation or separation of phases, in which the polymer making up the membrane is dissolved in a suitable solvent or vehicle of microencapsulation and the substance to be dissolved is suspended in this solution and kept in agitation.

The coacervation of the polymer around the substance to be coated is obtained in various manners, such as for example temperature variation, addition of another more soluble polymer in the vehicle, addition of a non solvent of the polymer constituting the membrane, etc. The membrane can be hardened and so the microcapsules are separated from the vehicle for example by filtration or centrifuging and finally drying.

In the pharmaceutical field, microencapsulation is used to mask unpleasant tastes, for slowing down the release of the drug, for preventing irritation arising from contact of the drugs with the gastrointestinal mucosa, for protecting drugs from degradation, for separating drugs which react with each other, for transforming the drug into a more easily used form, such as for example, converting it from a liquid state into a powder composed of microcapsules.

A common form of dosage for the oral administration of drugs, and especially of microencapsulated drugs, is that of monodose sachets. This moreover is the most convenient solution, if not the only one, if one must administer high doses of drugs. Monodose sachets containing microcapsules have been prepared in the past, sometimes also on an industrial scale, as cited in the volume "Microencapsulation" by J. R. Nixon, Chapter 7, page 93.

However they often present various disadvantages due especially to the hydrorepulsion of polymers making up the microcapsule membrane (for example polymers with a base of cellulose or waxy substances) and to the specific weight of the microencapsulated substances and therefore of the said microcapsules.

In fact when the contents of the sachets were poured out, as usual, in a glass of water or in fruit juice or in milk, the microcapsules formed a sediment on the bottom of the glass or floated on the surface, adhering partly to the walls of the said glass. This brought a notable inaccuracy to the quantity of the drug taken as well as poor acceptance by the patient who saw the particles floating or felt an unpleasant scraping sensation in the mouth or throat when swallowing the contents at the bottom of the glass where the mass of sedimented particles was found.

The addition of thickening substances could delay and maybe also eliminate the separation of the microcapsules, but in practice has given negative results because these substances tend to form lumps on contact with water which dissolve slowly and only by resorting to vigorous mechanical agitation. It was attempted to disperse these thickening substances together with other components of the formula by mixing them in the usual powder mixers. Also with this method the formation of lumps could not be avoided, but was only partly reduced.

The above mentioned difficulties were mainly solved by the invention described in Italian patent No. 1183574 which refers to a formulation, and a method for obtaining it, characterized in that:
1) a thickening agent is micronized
2) the thickening agent is suspended in an organic solution also containing a binding agent;
3) this suspension is applied by spraying it on to the surface of a substance which is easily soluble in water (sugar, sorbitol); and
4) the product obtained is dried and once mixed with the microcapsules and the flavourings is used for filling the monodose sachets.

When the contents of the sachets are poured in water and agitated, as described in the examples of the patents cited, in about 1 minute a homogeneous microcapsule suspension is obtained.

In practice however it is seen that the patients, after having poured the sachet contents into water, do not stir with a spoon for at least 60 seconds, but stop after 20–30 seconds at the most. After this time the thickener is still not sufficiently dissolved and so a homogeneous suspension is not obtained and the previously cited difficulties are only partially eliminated.

It is therefore considered necessary to find a system which reduces the mixing times. During the research carried out on this matter, most surprisingly it was found that if an acid and a base substance are added, the thickening of the liquid and the homogeneous suspension of the microcapsules is generally obtained by mixing for only 15–20 seconds.

According to the present invention there is provided a solid pharmaceutical composition for addition to water to produce a suspension of a drug comprising
 a) a drug which is substantially water-insoluble or microencapsulated;
 b) a thickening or suspending agent;
 c) a pharmaceutically acceptable acid;
 d) a pharmaceutically acceptable carbonate or bicarbonate; characterised in that the weight ratio of c+d:b is from 1:1.5 to 1:15 and the amount of c+d is sufficient to obtain rapid hydration of the thickening or suspending agent b) when the composition is mixed with water such that a homogeneous suspension of the drug is obtained within 30 seconds.

It is necessary however that the acid and base substances, are very thoroughly mixed with the thickening substance and therefore they must be soluble, or suspended in the form of micronized powder, in the organic solvent used for applying of the suspension containing the thickener.

With this invention the stirring time required is reduced by ⅓ to ¼ with respect to that of the prior art patent, making the product acceptable to the consumer and especially more easily and completely consumable.

It is important to note that the addition of an acidic substance and a base to the formulation is not done to obtain effervescence; in fact this is to be avoided, as seen experimentally, the formation of bubbles of carbon dioxide tends to carry afloat the granules coated with the thickening agent and delays the dissolution of this, giving rise to the opposite effect to that desired.

The quantity of carbon dioxide which is formed must therefore be just sufficient to keep the single particles separate from each other thus permitting a rapid hydration of the thickener.

Therefore, as determined experimentally, to obtain the desired effect, that is a rapid hydration of the thickener and brief mixing times, it is necessary that the base and acid substances are:
 thoroughly mixed with said thickener; this is obtained by dissolving them in the solvent in which the thickener is suspended, or in the event that these are not soluble by micronizing them to the same granulometry as the thickener and suspending them together with this;
 in a quantity so as not to allow effervescence but sufficient to obtaining the desired effect;
 in a suitable ratio with respect to each other and with the thickener.

As already cited the microcapsules can be prepared with various systems provided that the membrane which coats the drug to be constituted by a suitable polymer for pharmaceutical use.

The microcapsules will usually be comprised in weight of 3% to 50% polymer and from 50% to 97% drug. The polymer constituting the membrane must be permeable or soluble in the gastrointestinal juices in order to allow the release of the drug and its absorption.

The preferred polymer used is ethylcellulose, but as an illustrative and not limiting example polymers can also be cited such as for example polyacrylates, polymethacrylates, polyvinylchloride, polyvinylalcohol, polyethylene, polyamides, polysiloxanes, cellulose acetate phthalate, hydroxypropylmethylcellulose phthalate, polyvinyl acetate phthalate, hydroxypropylmethylcellulose acetate succinate, cellulose acetate trimellitate, copolymers of maleic acid, derivatives of phthalic acid, and also polymers of natural origin such as gelatine, arabic gum and Shellac.

With regard to the drugs contained in the microcapsules, any pharmacologically active substance whether in a liquid or powdery form, crystalline or granular form can be coated with polymeric membrane resorting to a suitable microencapsulation method. As an illustrative but not limiting example the following drugs are cited: theophylline, aminophylline, acethylsalicyclic acid, paracetamol, ibuprofen, cimetidine, dextromethorphan HBr, noscapine HCl, phenylephrine HCl, sodium dicloxacillin, sodium flucloxacillin, bacampicillin, metoclopramide, pseudoephedrine, ambroxol HCl.

With regard tot he quantity of the acid and base substances to be used it is preferable that the weight ratio between the sum of the quantities of these substances, acid or base, and the thickener is included between 1:1.5 and 1:15.

However with regard to the proportion to be used between the acid and base substances it is preferable that the weight ratio of the acid and base substances is included between 1:0.5 and 1:1.5.

Now the process which is the object of the invention is described. This consists of dispersing the thickening substance in the middle of the other components and preferably, but not limitatively, in sweetening agents, in a manner such that when the content of the monodose sachet is poured into water or in another aqueous medium there is a rapid dissolution of the thickening agent which, in 15-20 seconds confers sufficient viscosity to the medium to maintain the microcapsules in a homogeneous suspension in order to avoid the formation of lumps and especially separation of the microcapsules (floating and sedimentation).

The invention includes a method of preparing a pharmaceutical composition as described above comprising mixing b) a thickening or suspending agent c) a pharmaceutically acceptable acid, d) a pharmaceutically acceptable base selected from carbonates and bicarbonates and a) a water insoluble or microencapsulated drug wherein the ratio of c+d:b is from 1:1.5 to 1:15 and the amount of c+d is sufficient to obtain rapid hydration of the thickening or suspending agent b) when the composition is mixed with water such that a homogeneous suspension of the drug is obtained within 30 seconds.

The preferred process consists substantially of the following operations:
 1) Micronise, grind or anyway use the thickening substances with a granulometry less than 150 μm or better 75 μm;
 2) micronise, grind or anyway use an acid or base substance, not soluble in the solvent with the same granulometry as the thickening substance;
 3) suspend the thickening substance, in fine powder, in a solvent containing a binder; the thickener must be insoluble or at least one slightly soluble in the solvent in which the binding substance is dissolved; this, in turn, as well as obviously being soluble in the solvent, must also be soluble in water in order to "bind" the particles of the thickener to the support, but also to liberate them rapidly once in contact with the water;
 4) suspend or dissolve the base and acid substances, in the suspension cited in the previous point;
 5) apply the suspension thus obtained to granules or crystals of one or more components of the formulation to put in the monodose sachet.

Crystals or granules of one of the components of the formulation are placed in a suitable mixer, for example a planetary mixer, a coating pan, horizontal controtating ball mixer, a discontinuous mixer with vortex centrifuge, or similar. Preferably a sweetener is used for this is or another water soluble excipient just as other mixtures of the various components of the formulation can be used.

The suspension described in points 3) and 4) is then poured slowly or sprayed in the mixer in one or two phases. They are mixed in order to obtain a homogeneous distribution of the suspension around the granules or crystals of the solid excipient (s).

6) The product thus obtained is dried in an oven or in a fluid or in the said mixer. The solvent evaporates and the particles of thickener remain 'stuck' and homogeneously dispersed around the granules or crystals of solid excipient(s).

The product obtained is finally sieved.

As thickening substances of possible use, the following are cited as an illustrative but not limiting example: alginates, carrageenin, agar-agar, tragacanth gum, xanthan gum, guar gum, caroba gum, karaya gum, modified corn starch, carboxymethyl cellulose, crystalline cellulose alone or in combination with other hydrocolloids (e.g. AVICEL RC-591 of FMC Corporation). As binders the following are cited as illustrative but not limiting examples; methylcellulose, hydroxypropylmethylcellulose, hydroxyethylcellulose, hydroxy-propylcellulose, hydroxybutylcellulose, polyethyleneglycols, polyvinylalcohols, polyvinylpyrrolidone, gelatine, starches, modified starches, arabic gum.

As the inert excipients, to which the suspension containing the thickener can be applied, the following are cited as an illustrative but not limiting example, sucrose, lactose, fructose, mannitol, anhydrous sorbitol, maltodextrine, glycine, alanine, pentaerythrite.

As the acid substances, the following are cited as an illustrative but not limiting example: tartaric acid, citric acid, maleic acid, ascorbic acid, fumaric acid.

As the base substances, the following are cited as an illustrative but not limiting examples: sodium bicarbonate, potassium bicarbonate, sodium carbonate and other water soluble carbonic acid salts.

To facilitate the water penetration one can also add a surfactant; cited as an illustrative but not limiting example are: sodium dioctylsulfosuccinate, sodium laurylsulphate, various esters of sorbitol and sorbitans with fatty acids etc.

The surfactant can be added in any phase of the operation, even if it is preferable to add it in phase 3) of the above described process, or mix it in a micronized form with the other solid excipients.

The monodose sachets can be made in various materials, but that preferred, since it gives greater guarantee of impermeability, is aluminum foil together with paper and with a film of atoxic plastic and heat sealed material.

The monodose sachets are filled with a suitable machine using a loading tower in which the microencapsule mixture of the drug, the granules prepared with the above described process and the other excipients necessary for the final formulation, for example flavourings and colours are placed. Preferably however, for an improved dosage precision, machines with a double loading tower are used in which the microcapsules of the drug and the mixture of the other excipients are put into the sachet separately.

The following examples must be considered simply as illustrative of the procedure of this invention, without considering them as at all limiting of the object and scope of the said procedure.

EXAMPLE I

A) Preparation of the suspended granules Place 750 g of 95% ethyl alcohol in a 2 liter beaker.

Add 51 g of polyvinylpyrrolidone K30, 3 g of acid saccharin, 51 g of citric acid and keep stirring until completely in solution. Add, still stirring, 69 g of micronised sodium bicarbonate (granulometry less than 75 $\mu$m) and 210 g of xanthan gum having a granulometry less than 75 $\mu$m. Stir until a homogeneous suspension is obtained.

Apply this suspension to the surfaces of the sorbitol granules having a granulometry less than 700 $\mu$m.

To carry out this operation the suspension is poured on 2616 g of sorbitol granules placed in a counter-rotating horizontal ball mixer.

Dry the granulate for 14 hours at about 40° C. in a ventilation cupboard and sieve through a 700 $\mu$m mesh.

B) Preparation of the Monodose Sachets.

In a cube mixer, homogeneously mix 2000 g of the granules obtained in a) with 912 g of granulated sorbitol and 88.2 g of microcapsules of ambroxol HCl having an ethylcellulose membrane and titre of 850 mg/g.

Divide the mixture in monodose sachets of paper-/aluminium/heat sealed polythene.

3000 mg of mixture contain 75 mg of ambroxol HCl.

C) The content of a sachet is poured in half a glass of water (about 50 ml) and stirred with a teaspoon for about 15 seconds obtaining a homogeneous suspension suitable for taking.

EXAMPLE 2

A) Preparation of the suspended granules.

In a 2 liter beaker, place 1600 ml of 95% ethyl alcohol.

Add 72 g of polyvinylpyrrolidone K30, 4.5 g of acid saccharin, 77.7 g of tartaric acid and stir until completely in solution.

Add, still stirring, 55 g of ground potassium bicarbonate (granulometry less than 50 $\mu$m) and 1452 g of guar gum (granulometry less than 50 $\mu$m).

Stir until a homogeneous suspension is obtained.

Apply this suspension to the surfaces of granulated lactose having a granulometry less than 700 $\mu$m.

To carry out this operation place 700 g of granulated lactose in a laboratory mixer and mix with the suspension obtained previously.

Allow the granulate to dry under cover and sieve through a 700 $\mu$m mesh.

Dry the granulate for 14 hours at about 40° C. in a ventilation cupboard and eliminate the fraction at less than 250 $\mu$m.

B) Preparation of the monodose sachets

In a V mixer place 250 g of the granulate obtained in A), 50 g of granulated lactose, 97 g of ibuprofen microcapsules having a cellulose acetate phthalate membrane and titre of 909 mg/g, 1 g of talc and 2 g of mint flavouring.

Divide the mixture into monodose sachets made of paper/aluminium/heat sealed polythene.

4 g of the mixture contain 800 mg of ibuprofen.

C) The content of a sachet was poured into half a glass of water (about 50 ml) and stirred with a teaspoon for about 25 seconds obtaining a homogeneous suspension suitable to be taken.

EXAMPLE 3

A) Preparation of the suspended granules.

In a 5 liter beaker, place 2000 ml of 95% ethyl alcohol.

Add 120 g of polyvinylpyrrolidone K30, 72 g of anhydrous citric acid and stir until a complete solution is obtained.

Add, still stirring, 48 g of ground sodium bicarbonate (granulometry less than 100 μm) and 1200 g of xanthan gum (granulometry less than 100 μm).

Stir until a homogeneous suspension is obtained.

Apply this suspension to the surfaces of the sucrose granules having a granulometry between 210–700 μm.

To carry out this operation the suspension was sprayed on 8140 g of sucrose granules put in a flat-bottomed laboratory coating pan.

Dry the granulate in said coating pan and sieve through a 850 μm.

B) Preparation of monodose sachets.

In a cube mixer, place 2000 g of granules obtained in A), 620 g of granulated sucrose, 880 g of microcapsule potassium chloride (titre 860 mg/g, ethylcellulose membrane, P.R. 8:1) 0.5 g of talc, 1.5 g of cherry flavouring.

Divide the mixture into monodose sachets made of paper/aluminium/thermosealed polythene.

350 mg of mixture contain 750 mg of potassium chloride.

C) The contents of a sachet were poured into half a glass of water (about 50 ml) and stirred with a teaspoon for about 15 seconds obtaining a homogeneous suspension suitable to be taken.

EXAMPLE 4

A) Preparation of the suspended granules.

Place 250 ml of 95% ethyl alcohol in a 1 liter beaker.

Add 20 g of polyvinylpyrrolidone K30, 1 g of acid saccharin, 12.5 g of anhydrous citric acid and stir until completely in solution.

Add, while still stirring, 16.25 g of ground sodium bicarbonate (granulometry less than 50 μm) and 110 g of xanthan gum (granulometry less than 50 μm).

Apply this suspension to the surfaces of the sorbitol granules having a granulometry less than 700 μm.

Stir until a homogeneous suspension is obtained.

To carry out this operation the suspension was poured on 840 g of sorbitol granules put in a laboratory mixer. Dry the granules in a fluid bed and sieve through a 850 μmesh and eliminate the portion smaller than 250 μm.

B) Preparation of the monodose sachets.

In a cube mixer, place 200 g of the granules obtained in A), 1190 g of granulated sorbitol, 350 g of theophylline MIC (titre 860 mg/g, ethylcellulose membrane, P.R. 8:1), 10 g of talc, 50 g of strawberry flavouring.

Divide the mixture into monodose sachets made of paper/aluminium/thermosealed polythene.

3500 mg of mixture contain 300 mg of theophylline.

C) The contents of a sachet were poured into half a glass of water (about 50 ml) and stirred with a teaspoon for about 15 seconds obtaining a homogeneous suspension suitable to be taken.

EXAMPLE 5

To check the advantage of the method described in this invention with respect to the granules which are object of the Italian patent no 1183574, a granular suspension was prepared using the same method and the same excipients cited in example 3 in point A) but without citric acid and without sodium bicarbonate.

The monodose sachets were prepared using the same method and the same composition described in example 3 in point B).

The contents of these sachets were poured into the same quantity of water described in example 3 in point C) and mixed with a spoon: to obtain a homogeneous suspension it is necessary to mix for 55-75 seconds, that is a 3-4 times longer than that in example 3.

EXAMPLE 6

To check the advantage of the method described in this invention with respect to the monodose sachets prepared according to the usual methods, the excipients sachets prepared according to the usual methods, the excipients described in example 3, point A) i.e. 260 g of citric acid, 340 g of sodium bicarbonate and 1090 g of xanthan gum, are granulated with 170 g of polyvinylpyrrolidone in an alcoholic solution in order to obtain granules smaller than 700 μm.

This granulate was mixed with 8140 g of sucrose having a granulometry between 210 and 700 μm. The monodose sachets were prepared with the same method and the same composition described in example 3, point B).

The contents of these sachets were poured in the same quantity of water described in example 3, point C) and mixed with a spoon. It was found that to obtain a suspension of the microcapsules it is necessary to mix for more than 2 minutes and furthermore this suspension is not homogeneous but some lumps are present due to an irregular dispersion and hydration of the thickener.

We claim:

1. A solid pharmaceutical composition for addition to water to produce a suspension of a drug comprising a mixture of
   a) a drug which is substantially water-insoluble or microencapsulated; with granules comprising an inert carrier coated with an intimate mixture consisting essentially of
   b) a thickening or suspending agent;
   c) a pharmaceutically accepted acid;
   d) a pharmaceutically acceptable carbonate or bicarbonate; characterized in that the weight ratio of c+d:b is from 1:1.5 to 1:15 and the amount of c+d is sufficient to obtain rapid hydration of the thickening or suspending agent b) when the composition is mixed with water such that a homogeneous suspension of the drug is obtained within 30 seconds.

2. A composition as claimed in claim 1, wherein the weight ratio of c+d:b is from 1:1.5 to 1:5.

3. A composition as claimed in claim 1, wherein the weight ratio of c:d is from 1:0.5 to 1:1.5.

4. A composition as claimed in claim 1 wherein the acid is selected from the group consisting of tartaric, citric, pyruvic, maleic, ascorbic and fumaric acids.

5. As composition as claimed in claim 1, wherein the carbonate or bicarbonate d) is selected from the group consisting of sodium bicarbonate, potassium bicarbonate, sodium carbonate and other water soluble carbonic acid salts.

6. A composition as claimed in claim 1, wherein the thickening or suspending agent is selected from the group consisting of alginates, carrageenin, agar-agar, tragacanth gum, xanthan gum, guar gum, caroba gum, karaya gum, modified corn starch, carboxylmethylcellulose, crystalline cellulose, and mixtures thereof.

7. A composition as claimed in claim 1 wherein the composition contains a binding agent.

8. A composition is claimed in claim 7, wherein the binding agent is selected from the group consisting of methylcellulose, hydroxypropylmethylcellulose, hydroxyethylcellulose, hydroxypropylcellulose, hydroxybutylcellulose, polyethyleneglycol, polyvinyl alcohols, polyvinylpyrrolidone, gelatine, amides and modified amides.

9. A composition as claimed in claim 1 further comprising one or more excipients selected from the group consisting of sucrose, lactose, mannitol, anhydrous sorbitol, maltodextrine, glycine, alanine and pentaerythrite.

10. A composition as claimed in claim 1 comprising a surfactant.

11. A composition as claimed in claim 1 wherein a microencapsulated drug is used.

12. Sachets containing unit doses comprising a composition as claimed in claim 1.

13. A method for preparing a pharmaceutical composition which method comprises mixing granules comprising an inert carrier coated with an intimate mixture of b) a thickening or suspending agent, c) a pharmaceutically acceptable acid, d) a pharmaceutically acceptable base selected from the group consisting of carbonates and bicarbonates with a) a water insoluble or microencapsulated drug; wherein the ratio of c+d:b is from 1:1.5 to 1:15 and the amount of c+d is sufficient to obtain rapid hydration of the thickening or suspending agent b) when the composition is mixed with water such that a homogeneous suspension of the drug is obtained within 30 seconds.

14. A method as claimed in claim 13, wherein the thickening or suspending agent b) has the same granulometry as the acid c) and base d).

15. A method as claimed in claim 13, wherein the ingredients b, c and d are mixed in a non-aqueous solvent, then applied to a water soluble excipient and the mixture dried and then mixed with the drug.

16. A method as claimed in claim 14, wherein the granulometry is less than 150 μm.

17. A method as claimed in claim 13, wherein the ingredients b, c and d are mixed to form a homogeneous suspension in a non-aqueous solvent in which a binder is dissolved and in which the ingredient b) is substantially insoluble, the suspension is applied to a water soluble excipient and dried, then mixed with the drug.

18. A method as claimed in claim 17, wherein the excipient is selected from the group consisting of sucrose, lactose, fructose, mannitol, anhydrous sorbitol, maltodextrin, glycine, alanine and pentaerythrite.

19. A pharmaceutical composition prepared by the method described in claim 13.

* * * * *